(12) United States Patent
Bridgers (10) Patent No.: US 6,484,747 B2
(45) Date of Patent: Nov. 26, 2002

(54) MEDICAL GAS UTILITY STAND

(76) Inventor: Jerry S. Bridgers, 1353 Springhill Rd., Raymond, MS (US) 39154

(*) Notice: Subject to any disclaimer, the term of this patent is extended or adjusted under 35 U.S.C. 154(b) by 93 days.

(21) Appl. No.: 09/827,159

(22) Filed: Apr. 5, 2001

(65) Prior Publication Data

US 2002/0043595 A1 Apr. 18, 2002

Related U.S. Application Data

(60) Provisional application No. 60/194,751, filed on Apr. 5, 2000.

(51) Int. Cl.⁷ ............................................. F16L 37/28
(52) U.S. Cl. .................. 137/355.17; 137/343; 285/316; 128/204.18; 248/121; 248/129
(58) Field of Search .......................... 137/343, 355.17, 137/560; 285/316; 248/121, 129; 128/204.18, 205.24

(56) References Cited

U.S. PATENT DOCUMENTS

| | | | |
|---|---|---|---|
| 3,170,667 A | * | 2/1965 | Szohatzky |
| 4,344,455 A | * | 8/1982 | Norton et al. ............ 137/329.4 |
| 4,944,292 A | * | 7/1990 | Gaeke et al. ........... 128/204.18 |
| 5,038,819 A | * | 8/1991 | Sutphen ...................... 137/343 |
| 5,042,525 A | * | 8/1991 | Clark ........................... 137/381 |

* cited by examiner

Primary Examiner—A. Michael Chambers
(74) Attorney, Agent, or Firm—Needle & Rosenberg, PC.

(57) ABSTRACT

A medical gas utility stand for connection to at least one remote medical gas source, each medical gas source detachably connectable to a gas conduit line so that the gas conduit line is in fluid communication with one medical gas source. The gas utility stand includes a base connected to a substantially upright support member. The gas utility stand also includes a gas connection member having at least one gas conduit defining a gas passage extending between an input end and an output end, the gas connection member fixedly connected to the support member adjacent its top end. Additionally, the gas utility stand has at least one pair of identical gas fittings, each gas fitting defining a bore extending between an attachment end and a securing end, the securing ends of one pair of identical gas fittings detachably secured to the opposing input end and output end of one gas conduit so that the bores of the pair of identical gas fittings are in communication with the gas passage of the gas conduit. It is emphasized that this abstract is provided to comply with the rules requiring an abstract which will allow a searcher or other reader to quickly ascertain the subject matter of the technical disclosure. It is submitted with the understanding that it will not be used to interpret or limit the scope or meaning of the claims.

40 Claims, 7 Drawing Sheets

MEDICAL GAS UTILITY STAND

This application claims priority to the U.S. provisional application No. 60/194,751, filed Apr. 5, 2000, which is incorporated herein in its entirety.

SUMMARY OF THE INVENTION

Applicant's present invention is directed to a medical gas utility stand for connection to at least one remote medical gas source. The medical gas utility stand of the present invention allows for the remote gas sources, which are typically located the walls of hospital room, to be effectively organized and to be brought into proximity of the medical apparatuses that require the use of the various gases. The gas utility stand includes a base, a support member, a gas connection member and at least one pair of identical gas fittings. The base is in operative contact with a support surface such as a floor or the ground and is connected to the bottom end of the support member.

The gas connection member has at least one gas conduit having an input end and an opposing output end. The gas conduit defines a gas passage extending between the input end and the output end. The gas connection member is preferably fixedly connected to the support member near the top end of the support member. Each gas fitting has an attachment end and an opposing securing end and defines a bore extending between the attachment end and the securing end. The securing ends of one pair of identical gas fittings are detachably secured to the opposing input end and output end of one gas conduit so that the bores of the pair of identical gas fittings are in communication with the gas passage of the gas conduit.

Because different types of identical gas fittings can be secured to the input and output end of each gas conduit, the gas utility stand of the present invention advantageously allows a user to selectively choose any desired combination of medical gases desired by simply selecting the appropriate pair of identical gas fittings for each specific gas conduit. As one skilled in the art will appreciate, each gas fitting has a unique shape based upon a specific type of medical gas. Therefore, because of each gas fitting's unique shape, only medical accessories, medical equipment and/or gas conduit lines that are designed to utilize the specific medical gas may be detachably secured to the attachment end of a given gas fitting.

The gas utility stand may also have at least one gas conduit line. Each gas conduit line has a first end and a second end. Additionally, each gas line has a pair of gas connectors. One gas connector is fixedly attached to the first end and the other gas connector is fixedly attached to the second end of the gas conduit line. As one skilled in the art will appreciate, each gas connector has a shape that is complementary to the attachment end of one type of gas fitting. In operation, the gas connector at the first end of the gas conduit line is detachably connected to attachment end of one gas fitting that is secured within the input end of one gas conduit. Further, the gas connector at the second end of the gas conduit line is detachably connected to one medical gas source. Thus, the gas conduit line is in fluid communication with one medical gas source and, resultantly, the attachment end of the gas fitting that is detachably secured within the opposing output end of the gas conduit is in fluid communication with the one medical gas source. Because of the requirement that the shapes of the attachment end of the gas fitting and the gas connector be complementary for operable connection of the gas connector to the attachment end of the gas fitting, only the desired gas conduit line having the appropriate gas connectors can be detachable secured to a specific gas fitting. This ensures that only the desired medical gas from the medical gas source is supplied to the gas conduit.

In a second embodiment of the invention, the gas utility stand may also have a mounting plate that is detachably attached to the support member intermediate the base and the gas connection member. The mounting plate has a plurality of slide brackets for the detachable attachment of medical accessories.

In a third embodiment of the present invention, the gas utility stand may also include a hose bracket plate that is detachably attached to the support member intermediate the base and the gas connection member. The bracket plate has at least one pair of opposing toggle hangers that are connected to the front surface of the bracket plate. Each pair of opposing toggle switches define a pair of opposed slots so that a coil of the gas conduit line can be removably secured within the defined slots.

In a fourth embodiment of the present invention, the gas utility stand may also include both a mounting plate and a hose bracket plate as previously described. It is preferred that the mounting plate be detachably connected to the support member proximate the base and the bracket plate be detachably mounted to the support member intermediate the mounting plate and the gas connection member.

DETAILED DESCRIPTION OF THE FIGURES

DETAILED DESCRIPTION OF THE INVENTION

The present invention is more particularly described in the following examples that are intended to be illustrative only since numerous modifications and variations therein will be apparent to those skilled in the art. As used in the specification and in the claims, the singular form "a," "an" and "the" may include plural referents unless the context clearly dictates otherwise.

Referring first to FIGS. 1–4, the gas utility stand 10 of the present invention includes a base 12, a support member 20, a gas connection member 30 and at least one pair of identical gas fittings 40. The mobile medical gas utility stand 10 provides for remote gas sources 4, which are typically located the walls of hospital room, to be effectively organized and to be brought into proximity of the medical apparatuses that require the use of the various gases. It also allows for a user to customize the types of medical gases that can be subsequently brought into proximity of the desired medical apparatus.

The base 12 has an upper surface 14 and an opposed lower surface 16. The lower surface 16 of the base 12 is in operative contact with a support surface S such as a floor or the ground. The support member 20 has a top end 22, a bottom end 24, and a longitudinal length L extending between the top end 22 and the bottom end 24. The bottom end 24 of the support member 20 is connected to the upper surface 14 of the base 12. Preferably the support member 20 extends substantially upright. Further the support member 20 extends generally perpendicular to the upper surface 14 of the base 12 so that the longitudinal length L of the support member 20 extends substantially vertical relative to the substantially horizontal support surface S.

The gas connection member 30 has a first surface 32 and an opposing second surface 34. The gas connection member 30 also has at least one gas conduit 36 that extends through the gas connection member 30 from the first surface 32 to the second surface 34. Each gas conduit 36 has an input end 37 and an opposing output end 38. The gas conduit defines a gas passage 39 extending between the input end 37, and the output end 38. The gas connection member 30 is preferably fixedly connected to the support member 20 near the top end 22 of the support member 20. In one example, the gas connection member 20 may be fixedly connected to the top end 22 of the support member 20. Preferably, the gas connection member 30 is fixedly connected to the support member 20 so that the gas connection member 30 is substantially horizontal.

Figure 2:
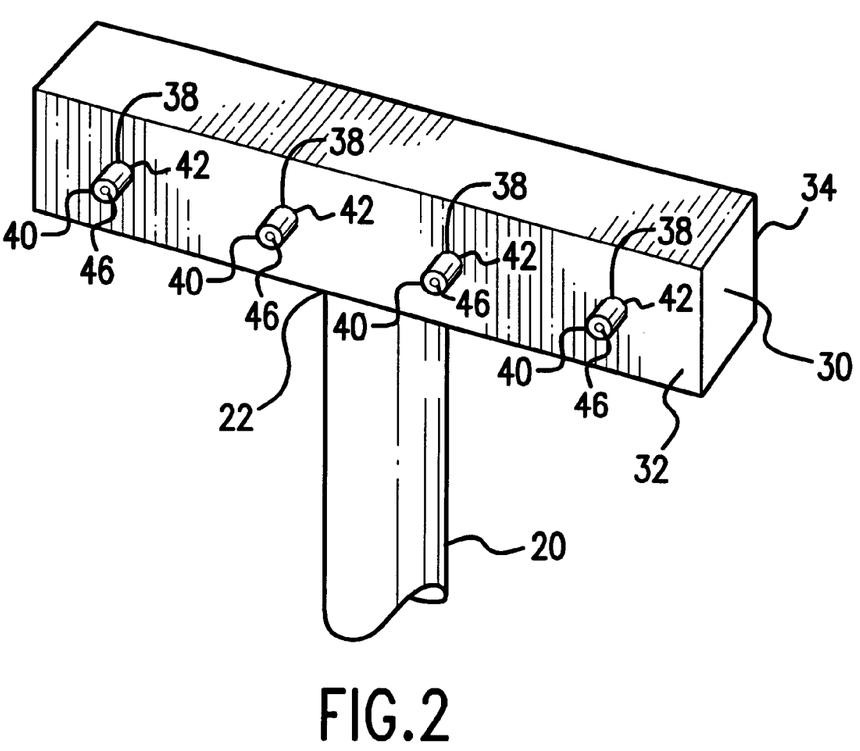
FIG. 2 is a partial perspective view of a gas connection member having a plurality of gas fittings detachably secured to an output end of a gas conduit.
Figure 3A:
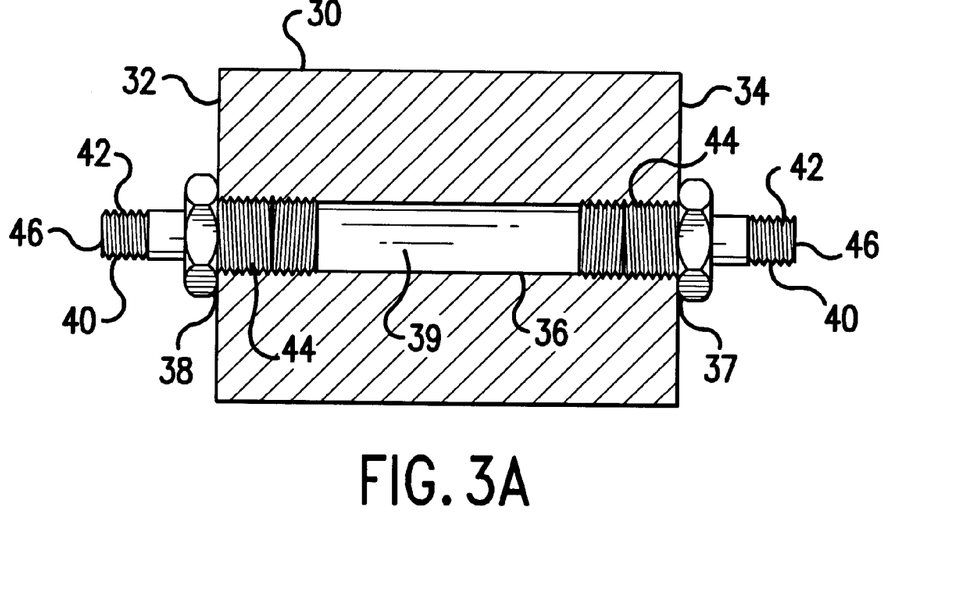
FIG. 3A is a partial cross-sectional view of a pair of identical gas fittings detachably secured within an input end and the output end of a gas conduit.
Figure 3B:
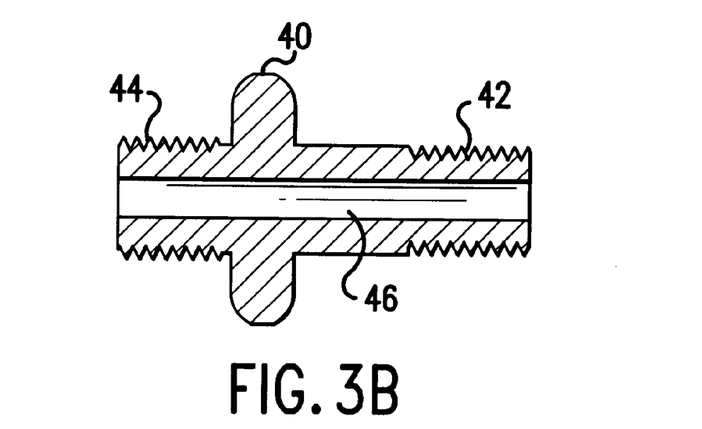
FIG. 3B is a cross-sectional view of a gas fitting showing an attachment end, a securing end, and a bore extending between the attachment end and the securing end.

Each gas fitting 40 has an attachment end 42 and an opposing securing end 44. Each gas fitting also defines a bore 46 that extends between the attachment end 42 and the securing end 44 of the gas fitting 40. The securing ends 44 of one pair of identical gas fittings 40 are detachably secured to the opposing input end 37 and output end 38 of one gas conduit 36 so that the bores 46 of the pair of identical gas fittings 40 are in communication with the gas passage 39 of the gas conduit 36.

Figure 4:
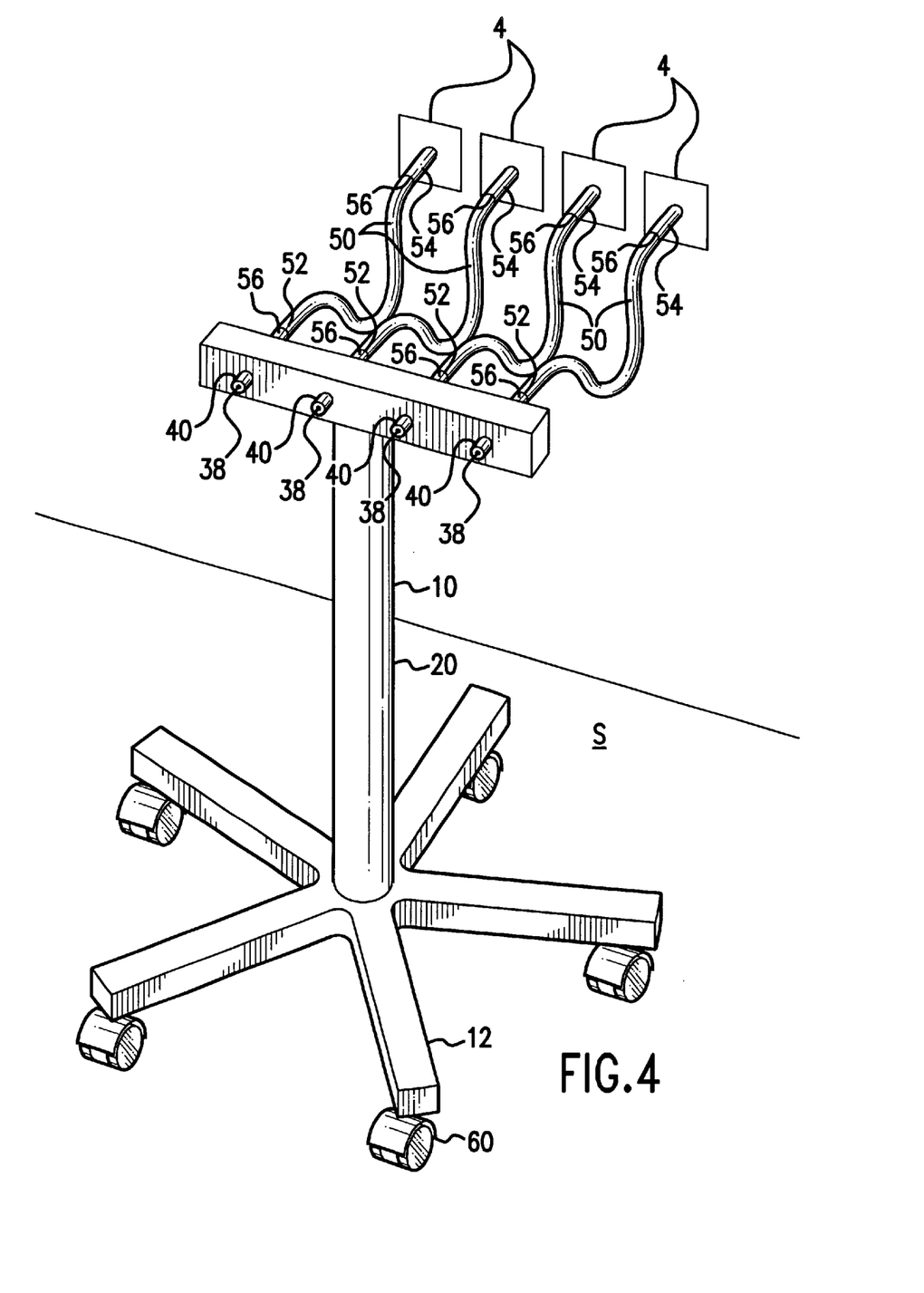
FIG. 4 is a perspective view of a first embodiment of the gas utility stand of the present invention showing a plurality of gas conduit lines in operable communication with a plurality of remote medical gas sources.

The present invention may also include at least one gas conduit line 50. Each gas conduit line has a first end 52, a second end 54, and a pair of gas connectors 56. One gas connector 56 is fixedly connected to the first end 52 and one gas connector 56 is fixedly connected to the second end 54 of the gas conduit line 50. As one skilled in the art will appreciate, each gas connector 56 has a shape that is complementary to the attachment end 42 of one type of gas fitting 40 so that the gas connector 56 at, for example, the first end 52 of the gas conduit line 50 can be detachably secured to the attachment end 42 of a gas fitting 40 that has a complementary exterior surface. Similarly, the gas connector 56 at, for example, the second end 54 of the gas conduit line 50 can be detachably secured to one medical gas source 4. This assures that desired gas conduit line 50 is in fluid communication with the desired medical gas source 4 and the appropriate attachment end 42 of the gas fitting 40 secured within the input end 37 of the desired gas conduit 36. Thus, the attachment end 42 of the gas fitting 40 that is detachably secured within the opposing output end 38 of the desired gas conduit 36 is brought into fluid communication with the desired medical gas 4.

It is preferred that the attachment end 42 of the gas fitting 40 have an exterior surface shape that will only allow engagement of medical devices or gas conduit lines 50 having a complementary shape. Thus for example, if the medical gas source 4 is oxygen, then the attachment end 42 of an "oxygen type" gas fitting 40 must have a unique surface shape that will only allow connection of gas conduit lines 50 with "oxygen type" gas connectors 56 having a complementary engagement surface. Because the attachment end 42 of the gas fitting 40 that is secured in the opposing output end 38 of the gas conduit 36 has the same unique surface shape, only medical apparatus or "oxygen type" gas connectors 56 having a complementary engagement surface can be secured to the attachment end 42. This safety feature prevents the connection of an inappropriate medical gas, inappropriate medical apparatus, and/or gas conduit line 50 to the pair(s) of identical gas fittings 40 secured to the gas connection member 30.

For example, the attachment end 42 of a gas fitting 40 may have a male fitting shape for complementary engagement of a female fitting of a gas connector 56 or a medical apparatus. The gas fittings 40 may be DISS fittings, and more preferably, may be male DISS fittings. If the gas fittings 40 are male DISS fitting, it is preferred that the complementary gas connector 56 is a female DISS fitting. The pairs of identical gas fittings 40 may, for example be, $O_2$ DISS fittings, Air DISS fittings, Vacumn DISS fittings, $N_2O$ DISS fittings, $N_2$ DISS fittings, Evacuation DISS fittings, and combinations of pairs of identical gas fittings 40 thereof. Alternatively, the pairs of identical gas fittings 40 may, for example be, $O_2$ male DISS fittings, Air male DISS fittings, Vacumn male DISS fittings, $N_2O$ male DISS fittings, $N_2$ male DISS fittings, Evacuation male DISS fittings, and combinations of pairs of identical gas fittings 40 thereof.

Because different types of identical gas fittings 40 can be secured to the input and output ends 37, 38 of each gas conduit 36, the gas utility stand 10 of the present invention advantagously allows a user to selectively choose any desired combination of medical gases that the user desires simply by selecting the appropriate pair of identical gas fittings 30 for each specific gas conduit 36. As noted above, because each gas fitting 40 has a unique shape based upon a specific type of medical gas, only medical accessories, medical equipment and/or gas conduit lines 50 that are designed to utilize the specific medical gas may be detachably secured to the attachment end 42 of a given gas fitting 40.

To detachably secure an individual gas fitting 40 to the input end 37 or the output end 38 of the gas conduit 36, the gas passage 39 of each gas conduit 36 preferably has a threaded surface at both the input end 37 and the output end 38 of the gas conduit 36. As one skilled in the art will appreciate, the securing end 44 of the gas fitting 40 has a complementarily threaded surface. Thus, in operation, the securing end 44 of one gas fitting 40 may be detachably secured within the input end 37, or output end 38, of the gas conduit 36 by threadedly securing the gas fitting 40 onto the provided threaded surface.

Figure 1:
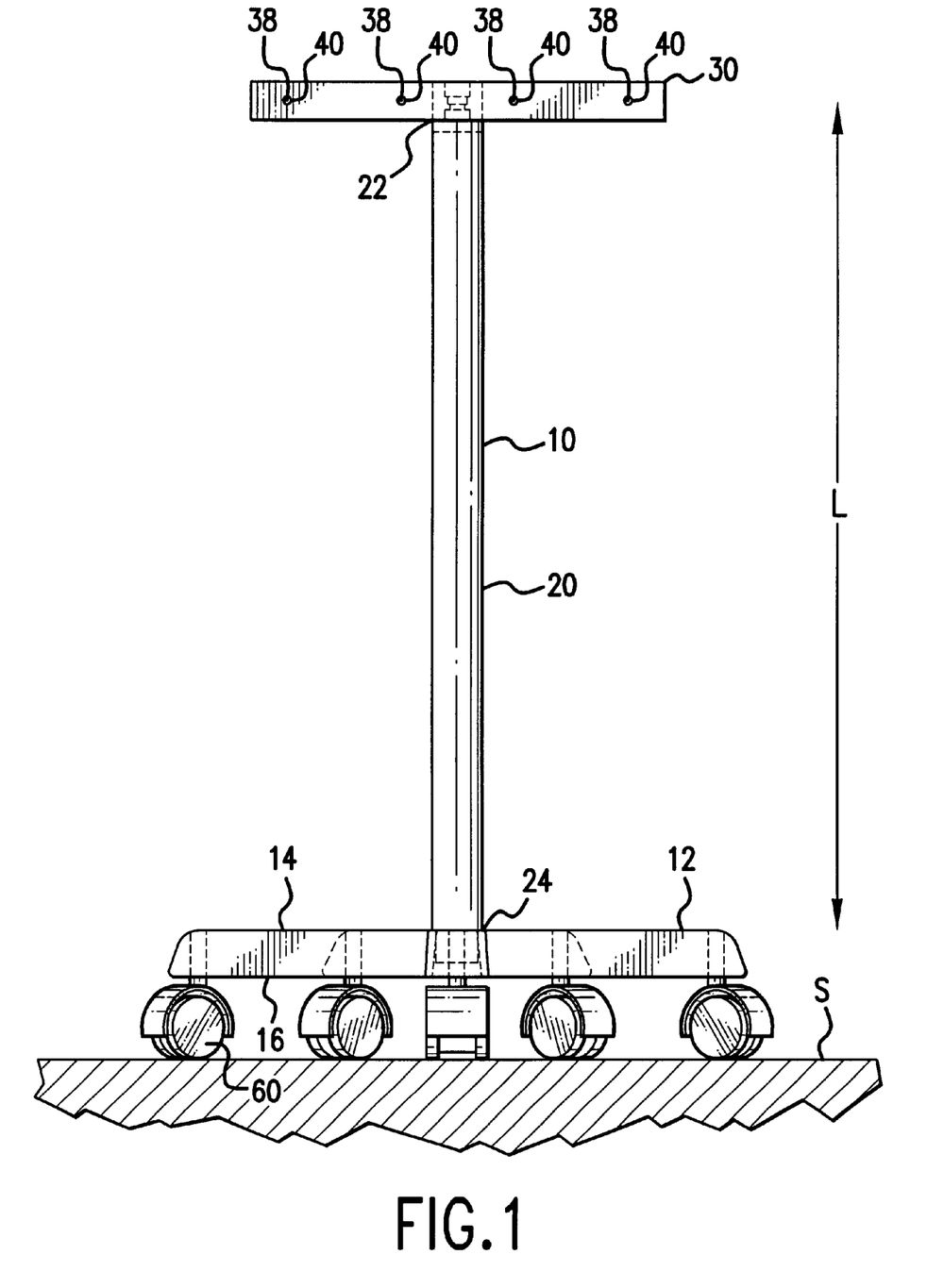
FIG. 1 is a front view of a first embodiment of the present invention.

The gas utility stand 10 may also have a plurality of casters 60 or rollers. These casters are connected to the lower surface 16 of the base 12 and are in contact with the support surface S. The casters 60 allow the gas utility stand 10 to be readily moved from one desired position to another with minimal effort. Exemplified casters 60 are well known to those skilled in the art.

Figure 5:
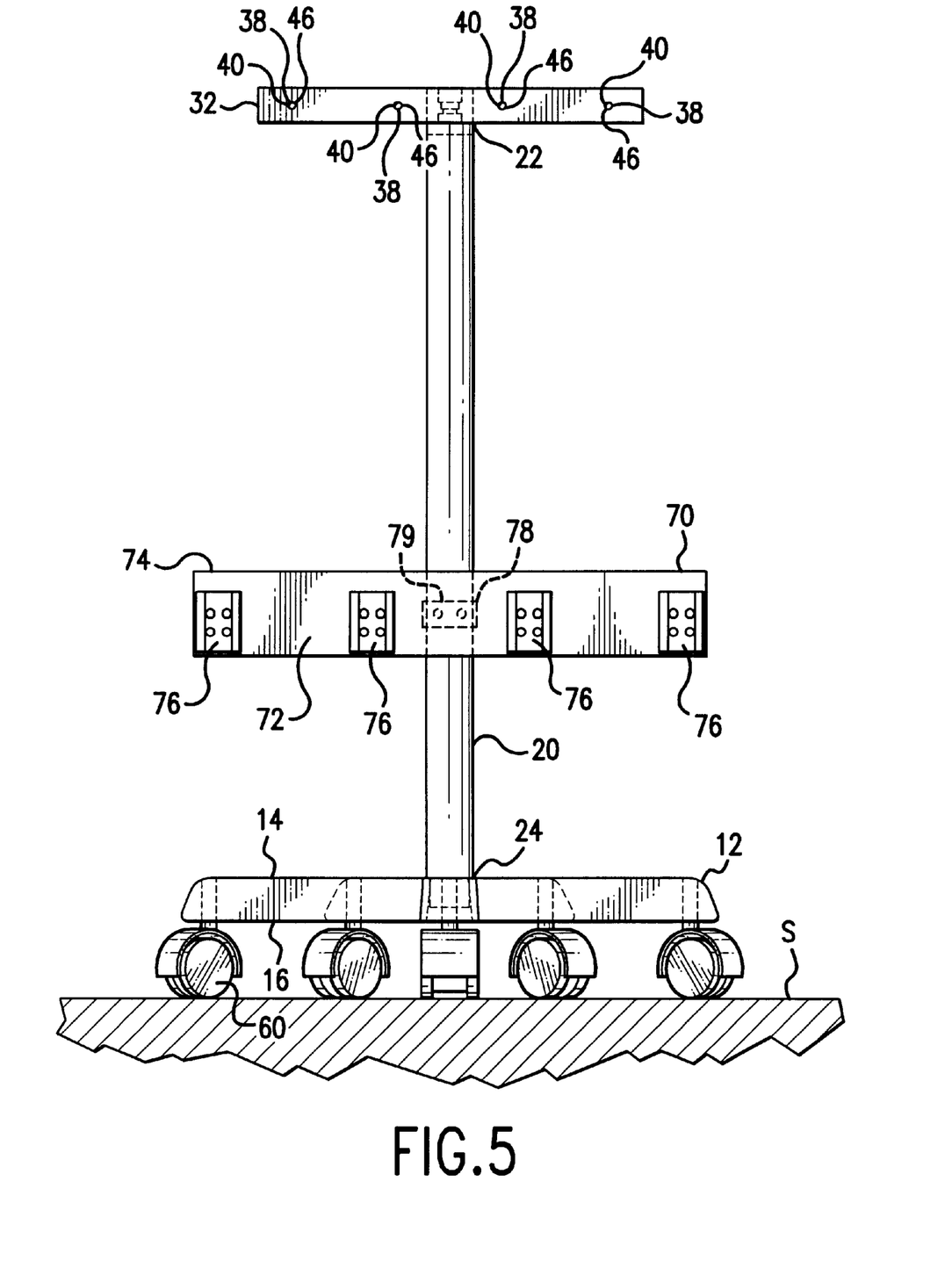
FIG. 5 is a front view of a second embodiment of the gas utility stand of the present invention.

The second embodiment of the gas utility stand 10 of the present invention is shown in FIG. 5. The construction of the second embodiment of the gas utility stand 10 is similar to the first embodiment and, accordingly, the figures use the same reference number for similar components. Furthermore, the components in FIG. 5 that use the same reference numbers as in FIGS. 1–4 are substantially equivalent and the description thereof is omitted for the second embodiment.

In the second embodiment of the invention, the gas utility stand 10 may also have a planar mounting plate 70 that is detachably attached to the support member 20 intermediate the base 12 and the gas connection member 30. The mounting plate 70 has a front surface 72, a back surface 74, and a plurality of slide brackets 76 for detachable attachment of medical accessories. It is preferred that each slide bracket 76 have a "U" shaped cross-section for the detachable attachment of medical accessories having a complementary engaging surface.

The mounting plate 70 further includes a clamp 78 for detachable connection of the mounting plate 70 to the support member 20. The clamp 78 is connected to the back surface 74 of the mounting plate 70 and defines a clamp bore 79 that extends parallel to the back surface 74 of the mounting plate 70. The clamp bore 79 is sized to complementarily engage the support member 20.

Figure 6:
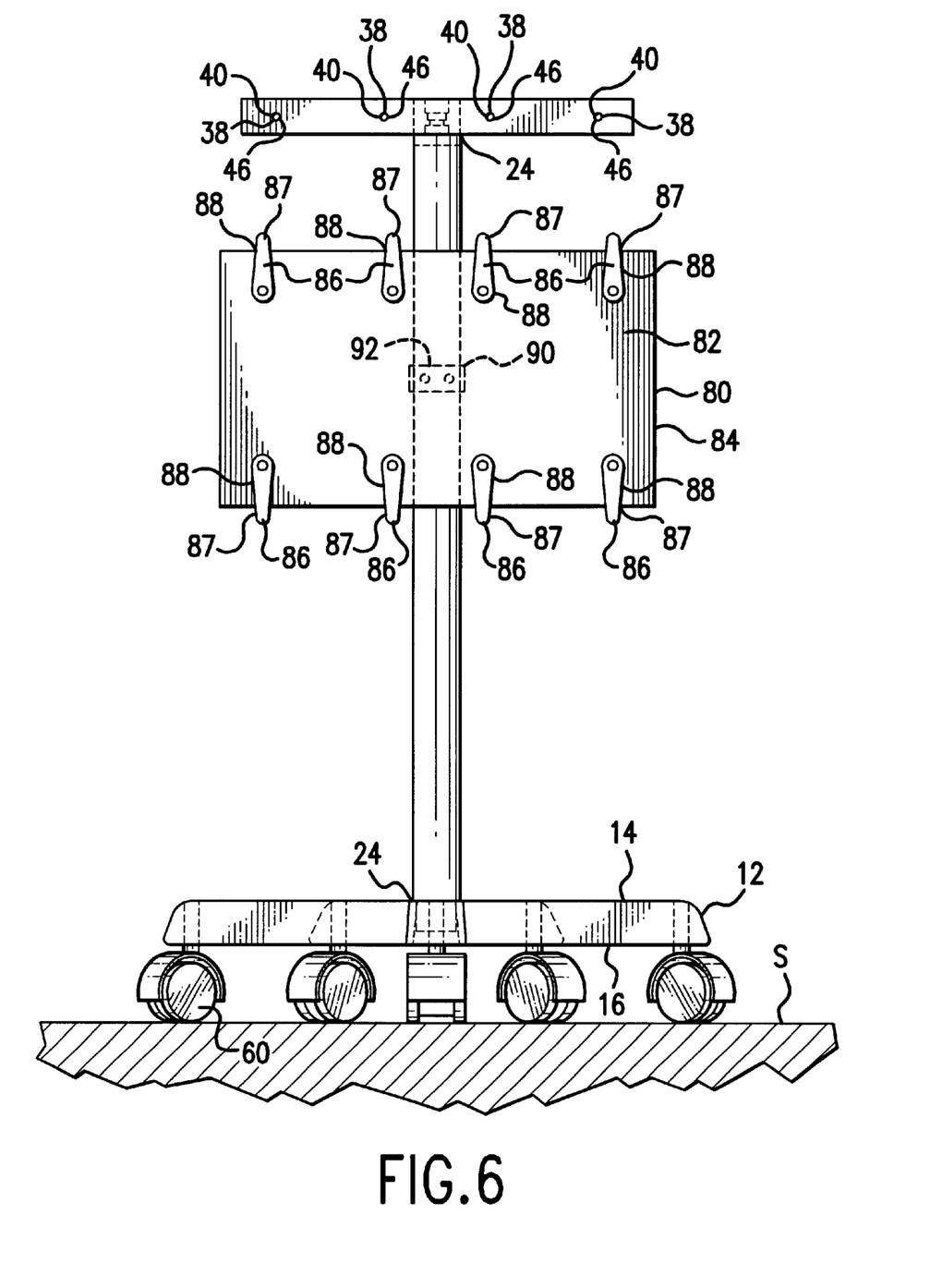
FIG. 6 is a front view of a third embodiment of the gas utility stand of the present invention.

The third embodiment of the gas utility stand 10 of the present invention is shown in FIG. 6. The construction of the third embodiment of the gas utility stand 10 is similar to the first embodiment and, accordingly, the figures use the same reference number for similar components. Furthermore, the components in FIG. 6 that use the same reference numbers as in FIGS. 1–4 are substantially equivalent and the description thereof is omitted for the third embodiment.

In the third embodiment of the present invention, the gas utility stand 10 may also include a hose bracket plate 80 that is detachably attached to the upright support member 20 intermediate the base 12 and the gas connection member 30. The bracket plate 80 has a front bracket surface 82 and a back bracket surface 84. Additionally, the bracket plate 80 has at least one pair of opposing toggle hangers 86 that are fixedly connected to the front bracket surface 82 of the bracket plate 80.

Preferably, each toggle hanger 87 has a "L" shape in cross-section. As will be appreciated, other cross-sectional surfaces are contemplated, such as, for example, a "C" shape, a "U" shape, a hook shape, and the like. Each toggle hanger 87 of each pair of opposing toggle hangers 86 extends outwardly and away from its opposing toggle hanger 87 to define, as one skilled in the art will appreciate, a slot 88 between each toggle hanger 87 and the front bracket surface 82 of the bracket plate 80. As one skilled in the art will further appreciate, a gas conduit line 50 may be coiled within the defined slots 88 of one pair of opposing toggle hangers 86 so that a coil of the gas conduit line 50 can be removably secured within the defined slots 88.

The hose bracket plate 80 further includes a bracket clamp 90. The bracket clamp 90 is connected to the back bracket surface 84 of the bracket plate 80 and defines a bracket clamp bore 92 that extends parallel to the back bracket surface 84 of the bracket plate 80. The bracket clamp bore 92 is sized to complementarily engage the support member 20 for detachable connection of the bracket plate 80 to the support member 20.

Figure 7:
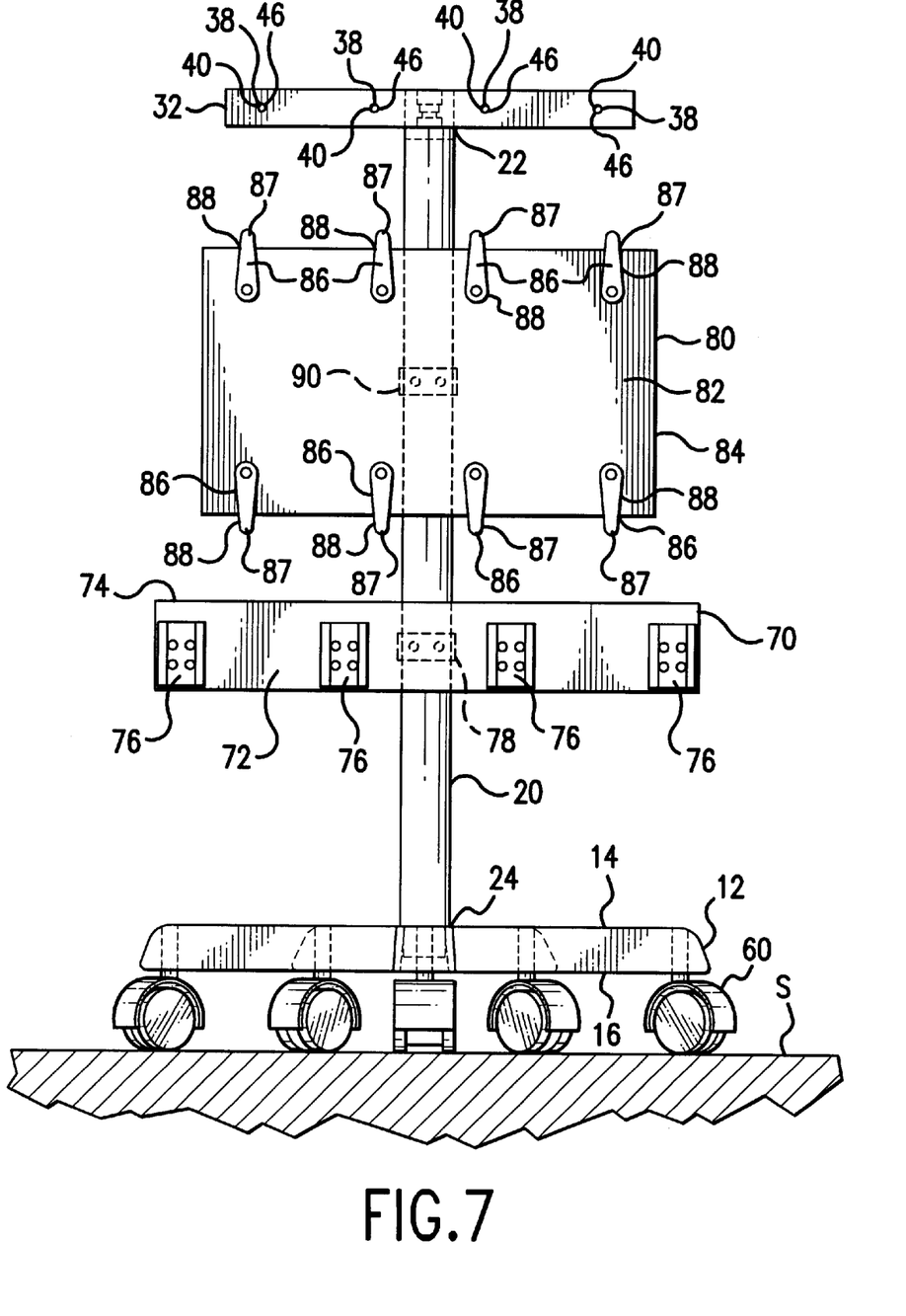
FIG. 7 is a front view of a fourth embodiment of the gas utility stand of the present invention.

The fourth embodiment of the gas utility stand 10 of the present invention is shown in FIG. 7. The construction of the second embodiment of the gas utility stand is similar to the first, second, and third embodiments and, accordingly, the figures use the same reference number for similar components. Furthermore, the components in FIG. 7 that use the same reference numbers as in FIGS. 1–6 are substantially equivalent and the description thereof is omitted for the fourth embodiment.

In the fourth embodiment of the present invention, the gas utility stand 10 may also include both a mounting plate 70 and a hose bracket plate 80 as previously described. It is preferred that the mounting plate 70 be detachably connected to the support member 20 proximate the base 12 and the bracket plate 80 be detachably mounted to the support member 20 intermediate the mounting plate 70 and the gas connection member 30.

Regardless of the embodiment, the gas utility stand 10 of the present invention is preferably formed of a non-ferrous material. More preferably, the gas utility stand 10 is formed of a non-ferrous and non-conductive material. This allows the gas utility stand 10 to be used in close proximity to a MRI and/or an IMRI. Examples of suitable materials include rigid polymers, or aluminum, for example, anodized aluminum.

Although the present invention has been described with reference to specific detail of certain embodiments thereof, it is not intended that such details should be regarded as limitations upon the scope of the invention except as and to the extent that they are included in the accompanying claims.

What is claimed is:

1. A medical gas utility stand comprising:
 a) a base having an upper surface and an opposed lower surface;
 b) a support member having a top end, a bottom end, and a longitudinal length extending between the top end and the bottom end, the bottom end connected to the upper surface of the base so that the support member extends substantially upright therefrom;
 c) a gas connection member having a first surface, an opposing second surface, and at least one gas conduit having an input end and an opposing output end and defining a gas passage extending between the input end and the output end, the gas conduit extending through the gas connection member from the first surface to the second surface, the gas connection member fixedly connected to the support member adjacent its top end; and
 d) at least one pair of identical gas fittings, each gas fitting having an attachment end and an opposing securing end and defining a bore extending between the attachment end and the securing end, the securing ends of one pair of identical gas fittings detachably secured to the opposing input end and output end of one gas conduit so that the bores of the pair of identical gas fittings are in communication with the gas passage of the gas conduit,
 wherein the base, the support member, the gas connection member, and the pair of identical gas fittings are formed from a non-ferrous material.

2. The gas utility stand of claim 1, wherein the base, the support member, the gas connection member, and the pair of identical gas fittings are formed from a non-conductive material.

3. The gas utility stand of claim 2, wherein the base, the support member, the gas connection member, and the pair of identical gas fittings are formed from materials selected from a group consisting of a rigid polymer and aluminum.

4. The gas utility stand of claim 1, further comprising at least one gas conduit line, each gas conduit line having a first end and a second end and having a pair of gas connectors, each gas connector fixedly attached to the first end and the second end of the gas conduit line, each gas connector having a shape complementary to the attachment end of at least one gas fitting, wherein the first end of the gas conduit line is detachably connected to the attachment end of one gas fitting that is secured within the input end of one gas conduit.

5. The gas utility stand of claim 4, wherein the second end of the gas conduit line detachably connected to one medical gas source so that the gas conduit line is in fluid communication with a medical gas source so that the attachment end of the gas fitting detachably secured within the opposing output end of the gas conduit is in fluid communication with one medical gas source.

6. The gas utility stand of claim 1, wherein the attachment end of the gas fitting has an exterior surface shape that will only allow engagement of medical devices or gas conduit lines having a complementary engagement surface shape.

7. The gas utility stand of claim 6, wherein the attachment end of the gas fitting has a male fitting shape for complementary engagement of a female fitting.

8. The gas utility stand of claim 4, wherein each gas connector has a female fitting shape for complementary engagement to the attachment end of the gas fitting.

9. The gas utility stand of claim 7, wherein the pair of identical gas fittings are male DISS fittings.

10. The gas utility stand of claim 9, wherein the pair of identical gas fittings are selected from the group consisting of: $O_2$ male DISS fittings, Air male DISS fittings, Vacumn male DISS fittings, $N_2O$ male DISS fittings, $N_2$ male DISS fittings, Evacuation male DISS fittings, and combinations of pairs of identical gas fittings thereof.

11. The gas utility stand of claim 8, wherein each gas connector is a female DISS fitting.

12. The gas utility stand of claim 1, wherein the gas passage of each gas conduit has a threaded surface at both the input end and the output end of the gas conduit, and wherein the securing end of the gas fitting has a complementarily threaded surface so that the securing end of the gas fittings are detachably securable within the input end and the output end of the gas conduits.

13. The gas utility stand of claim 1, further comprising a plurality of casters connected to the lower surface of the base and in contact with a support surface.

14. The gas utility stand of claim 1, further comprising a mounting plate having a front surface, a back surface, and a plurality of slide brackets, the mounting plate detachably connected to the support member intermediate the base and the gas connection member, the plurality of slide brackets attached to the front surface in a substantially upright orientation.

15. The gas utility stand of claim 1, further comprising a hose bracket plate having a front bracket surface, a back bracket surface, and at least one pair of opposing toggle hangers for detachable attachment of one gas conduit line for each pair of opposing toggle hangers, the hose bracket plate detachably connected to the support member intermediate the base and the gas connection member, each pair of opposing toggle hangers connected to the front surface of the bracket plate.

16. A medical gas utility stand comprising:
a) a base having an upper surface and an opposed lower surface;
b) a support member having a top end, a bottom end, and a longitudinal length extending between the top end and the bottom end, the bottom end connected to the upper surface of the base so that the support member extends substantially upright therefrom;
c) a gas connection member having a first surface, an opposing second surface, and at least one gas conduit having an input end and an opposing output end and defining a gas passage extending between the input end and the output end, the gas conduit extending through the gas connection member from the first surface to the second surface, the gas connection member fixedly connected to the support member adjacent its top end; and
d) at least one pair of identical gas fittings, each gas fitting having an attachment end, an opposing securing end, and defining a bore extending between the attachment end and the securing end, the securing ends of one pair of identical gas fittings detachably secured to the opposing input end and output end of one gas conduit so that the bores of the pair of identical gas fittings are in communication with the gas passage of the gas conduit,
wherein the attachment end of the gas fitting that is detachably secured within the input end of the gas conduit is detachably secured to one gas conduit line so that the attachment end of the gas fitting detachably secured within the opposing output end of the gas conduit is in fluid communication with one medical gas source.

17. The gas utility stand of claim 16, wherein the attachment end of the gas fitting has an exterior surface shape that will only allow engagement of medical devices or gas conduit lines having a complementary engagement surface shape.

18. The gas utility stand of claim 17, wherein the pair of identical gas fittings are DISS fittings.

19. The gas utility stand of claim 18, wherein the pair of identical gas fittings are selected from the group consisting of: $O_2$ DISS fittings, Air DISS fittings, Vacumn DISS fittings, $N_2O$ DISS fittings, $N_2$ DISS fittings, Evacuation DISS fittings, and combinations of pairs of identical gas fittings thereof.

20. The gas utility stand of claim 16, wherein the gas passage of each gas conduit has a threaded surface at both the input end and the output end of the gas conduit, and wherein the securing end of the gas fitting has a complementarily threaded surface so that the securing end of the gas fittings are detachably securable within the input end and the output end of the gas conduits.

21. The gas utility stand of claim 16, further comprising a plurality of casters connected to the lower surface of the base and in contact with a support surface.

22. The gas utility stand of claim 16, further comprising a mounting plate having a front surface, a back surface, and a plurality of slide brackets, the mounting plate detachably connected to the support member intermediate the base and the gas connection member, the plurality of slide brackets attached to the front surface in a substantially upright orientation.

23. The gas utility stand of claim 22, wherein the slide brackets have a U-shape in cross-section.

24. The gas utility stand of claim 22, wherein the mounting plate further comprises a clamp, the clamp is connected to the back surface of the mounting plate and defines a clamp bore that extends parallel to the back surface of the mounting plate, the clamp bore sized to complementarily engage the support member so that the mounting plate may be detachably connected to the support member.

25. The gas utility stand of claim 16, further comprising a hose bracket plate having a front bracket surface, a back bracket surface, and at least one pair of opposing toggle hangers for detachable attachment of one gas conduit line for each pair of opposing toggle hangers, the hose bracket plate detachably connected to the support member intermediate the base and the gas connection member, each pair of opposing toggle hangers connected to the front surface of the bracket plate.

26. The gas utility stand of claim 25, wherein each toggle hanger has a L-shape in cross-section, wherein each toggle hanger of each pair of opposing toggle hangers extends outwardly and away from its opposing toggle hanger to define a slot between toggle hanger and the front bracket surface of the hose bracket plate.

27. The gas utility stand of claim 26, wherein the hose bracket plate further comprises a bracket clamp, the bracket clamp connected to the back bracket surface of the hose bracket plate and defines a bracket clamp bore that extends parallel to the bracket back surface of the hose bracket plate, the bracket clamp bore sized to complementarily engage the support member so that the hose bracket plate is detachably connected to the upright support member.

28. A medical gas utility stand comprising:
   a) a base having an upper surface and an opposed lower surface;
   b) a support member having a top end, a bottom end, and a longitudinal length extending between the top end and the bottom end, the bottom end connected to the upper surface of the base so that the support member extends substantially upright therefrom;
   c) a gas connection member having a first surface, an opposing second surface, and at least one gas conduit having an input end and an opposing output end and defining a gas passage extending between the input end and the output end, the gas conduit extending through the gas connection member from the first surface to the second surface, the gas connection member fixedly connected to the support member adjacent its top end;
   d) at least one pair of identical gas fittings, each gas fitting having an attachment end and an opposing securing end and defining a bore extending between the attachment end and the securing end, the securing ends of one pair of identical gas fittings detachably secured to the opposing input end and output end of one gas conduit so that the bores of the pair of identical gas fittings are in communication with the gas passage of the gas conduit; and
   e) at least one gas conduit line, each gas conduit line having a first end and a second end and having a pair of gas connectors, each gas connector fixedly attached to the first end and the second end of the gas conduit line, each gas connector having a shape complementary to the attachment end of at least one gas fitting, the first end of the gas conduit line detachably connected to the attachment end of one gas fitting that is secured within the input end of one gas conduit and the second end of the gas conduit line detachably connected to one medical gas source so that the gas conduit line is in fluid communication with a medical gas source so that the attachment end of the gas fitting detachably secured within the opposing output end of the gas conduit is in fluid communication with the medical gas source.

29. The gas utility stand of claim 28, wherein the attachment end of the gas fitting has an exterior surface shape that will only allow engagement of medical devices or gas conduit lines having a complementary engagement surface shape.

30. The gas utility stand of claim 28, wherein the attachment end of the gas fitting has a male fitting shape for complementary engagement of a female fitting.

31. The gas utility stand of claim 30, wherein each gas connector has a female fitting shape for complementary engagement to the attachment end of the gas fitting.

32. The gas utility stand of claim 30, wherein the pair of identical gas fittings are male DISS fittings.

33. The gas utility stand of claim 32, wherein the pair of identical gas fittings are selected from the group consisting of: $O_2$ male DISS fittings, Air male DISS fittings, Vacumn male DISS fittings, $N_2O$ male DISS fittings, $N_2$ male DISS fittings, Evacuation male DISS fittings, and combinations of pairs of identical gas fittings thereof.

34. The gas utility stand of claim 31, wherein each gas connector is a female DISS fitting.

35. The gas utility stand of claim 28, wherein the gas passage of each gas conduit has a threaded surface at both the input end and the output end of the gas conduit, and wherein the securing end of the gas fitting has a complementarily threaded surface so that the securing end of the gas fittings are detachably secureable within the input end and the output end of the gas conduits.

36. The gas utility stand of claim 28, further comprising a plurality of casters connected to the lower surface of the base and in contact with a support surface.

37. The gas utility stand of claim 28, further comprising a mounting plate having a front surface, a back surface, and a plurality of slide brackets, the mounting plate detachably connected to the support member intermediate the base and the gas connection member, the plurality of slide brackets attached to the front surface in a substantially upright orientation.

38. The gas utility stand of claim 37, wherein the mounting plate further comprises a clamp, the clamp is connected to the back surface of the mounting plate and defines a clamp bore that extends parallel to the back surface of the mounting plate, the clamp bore sized to complementarily engage the support member so that the mounting plate is detachably connected to the support member.

39. The gas utility stand of claim 28, further comprising a hose bracket plate having a front bracket surface, a back bracket surface, and at least one pair of opposing toggle hangers for detachable attachment of one gas conduit line for each pair of opposing toggle hangers, the hose bracket plate detachably connected to the support member intermediate the base and the gas connection member, each pair of opposing toggle hangers connected to the front surface of the bracket plate.

40. The gas utility stand of claim 39, wherein the hose bracket plate further comprises a bracket clamp, the bracket clamp connected to the back bracket surface of the hose bracket plate and defines a bracket clamp bore that extends parallel to the bracket back surface of the hose bracket plate, the bracket clamp bore sized to complementarily engage the support member so that the hose bracket plate is detachably connected to the support member.

* * * * *